United States Patent
Kleen

(10) Patent No.: US 7,309,160 B2
(45) Date of Patent: Dec. 18, 2007

(54) METHOD AND ARRANGEMENT FOR X-RAY EXAMINATION

(75) Inventor: Martin Kleen, Furth (DE)

(73) Assignee: Siemens Aktiengesellschaft, Munich (DE)

( * ) Notice: Subject to any disclaimer, the term of this patent is extended or adjusted under 35 U.S.C. 154(b) by 150 days.

(21) Appl. No.: 11/333,652

(22) Filed: Jan. 17, 2006

(65) Prior Publication Data

US 2006/0184017 A1  Aug. 17, 2006

(30) Foreign Application Priority Data

Jan. 17, 2005  (DE) .................. 10 2005 002 191

(51) Int. Cl.
*G01D 18/00* (2006.01)
(52) U.S. Cl. .................. 378/207; 378/63; 600/411
(58) Field of Classification Search ............. 378/62, 378/63, 65, 113, 137, 138, 207; 600/407, 600/410, 411, 425, 466
See application file for complete search history.

(56) References Cited

U.S. PATENT DOCUMENTS

| 5,065,420 A | 11/1991 | Levene | 378/137 |
|---|---|---|---|
| 5,713,357 A | 2/1998 | Meulenbrugge et al. | 600/411 |
| 2003/0144590 A1 | 7/2003 | Maschke | 600/425 |
| 2004/0101110 A1 | 5/2004 | Eppler | 378/207 |
| 2004/0242995 A1 | 12/2004 | Maschke | 600/424 |

FOREIGN PATENT DOCUMENTS

| DE | 40 23 490 C2 | 1/1991 |
|---|---|---|
| DE | 695 30 558 T2 | 6/1996 |
| DE | 102 03 372 A1 | 9/2003 |
| DE | 103 38 742 A1 | 6/2004 |
| DE | 103 13 868 A1 | 10/2004 |

*Primary Examiner*—Courtney Thomas

(57) ABSTRACT

In order during an x-ray examination, despite a variable foreign magnetic field at the location of an x-ray tube to still enable x-ray images with image sections giving the same coverage to be generated, there is provision in accordance with the invention to compensate for the previously determined change to the foreign magnetic field at the location of the x-ray tube by a correspondingly controlled opposing magnetic field; Advantageously at least one compensating magnet is provided for this purpose which can be assigned to the x-ray tube and is controllable by a processing unit depending on this change.

20 Claims, 4 Drawing Sheets

METHOD AND ARRANGEMENT FOR X-RAY EXAMINATION

CROSS REFERENCE TO RELATED APPLICATIONS

This application claims priority to the German application No. 10 2005 002 191.3, filed Jan. 17, 2005 which is incorporated by reference herein in its entirety.

FIELD OF INVENTION

The invention relates to a method or an arrangement for x-ray examination with an x-ray tube in a variable foreign magnetic field, especially for extracorporeal magnetic navigation of an intracorporeal catheter.

BACKGROUND OF INVENTION

During an x-ray examination electrons in the form of an electron beam are accelerated in an x-ray tube towards an anode and form a focus there which represents the source of the x-ray radiation, In a magnetic navigation of a catheter in blood vessels or in the heart of a patient or a laboratory animal known from DE 103 13 868 A, such an x-ray tube is operated during the x-ray examination in the variable foreign magnetic field necessary for navigation; In this way the electron beam is deflected by the foreign magnetic field so that the focus on the anode shifts and the x-ray radiation thus appears in a modified geometric image at an x-ray detector or an x-ray film In x-ray examination methods in which a number of x-ray images are created and evaluated against each other, the variable foreign magnetic field, despite an unchanged relative position of x-ray tube, examination object and x-ray detector or x-ray film, leads to image sections of the x-ray images offset against each other in each case.

SUMMARY OF INVENTION

The x-ray examination method described below for optical checking of the previously mentioned navigation of a catheter through blood vessels or through the heart by means of a strong external foreign magnetic field is particularly relevant to the above-mentioned problem. First of all an x-ray image of the blood vessel and the heart is generated by means of digital subtraction angiography with the aid of a contrast means. While the catheter is being guided through the blood vessel or the heart with the aid of the foreign magnetic field, fluoroscopy x-ray images are generated for ongoing checking of the catheter position. From an overlaying of the relevant fluoroscopy x-ray image with the original x-ray image created by means the digital subtraction angiography the relevant position of the catheter in the blood vessels or in the heart can be determined. The change in the magnetic field during navigation causes the fluoroscopy x-ray images to shift relative to the original x-ray image created by means of digital subtraction angiography so that the two image sections of the x-ray images no longer coincide, the position of the catheter can no longer be uniquely determined and a safe navigation of the catheter is not possible. Thus the use of magnetic navigation is limited to medical specialist areas in which it is possible to dispense with an x-ray image created prior to navigation, especially one created by means of digital subtraction angiography.

An object of the invention is, for an x-ray examination of the type mentioned above, despite a variable magnetic field at the location of an x-ray tube, to enable x-ray images to be created with the same coverage in their image sections.

This object is achieved by the claims.

This change at the location of the x-ray tube can be compensated for through the opposing magnetic field controlled in accordance with the change in the foreign magnetic field, so that the image sections of x-ray images recorded at different times still cover the same area, despite a change in the foreign magnetic field which temporarily has to be taken into account. In the above-mentioned x-ray examination method provided for optical checking of the navigation of a catheter, the invention makes possible a fluoroscopy image covering the same area during the entire examination as an x-ray image created before the navigation, especially by means of digital subtraction angiography, so that the position of the catheter can be easily detected despite the foreign magnetic field necessary for navigation and thus the catheter can be safely navigated. The inventive solution expands the area of application of magnetic navigation to x-ray examination methods in which, especially with the aid of digital subtraction angiography an x-ray image is initially created to which further x-ray images of the same image section created during magnetic navigation are related.

An exclusively passive screening of the x-ray tube is not sufficient to resolve this problem.

To create the opposing magnetic field in a technically simple manner, there is provision in accordance with an advantageous embodiment for at least one compensation magnet controlled in accordance with the change to the foreign magnetic field determined, especially simultaneously with this change.

With a change to the foreign magnetic field controlled by control data of a control means, especially in the form of a computer, the change in the foreign magnetic field at the location of the x-ray tube takes especially little effort to determine by accessing this control data, since in addition to the control data that is already available, only the geometrical position of the x-ray tube relative to the foreign magnetic field has to be taken into account.

For an especially accurate determination of the change to the magnetic field at the location of the x-ray tube at least one magnetic field sensor is provided, especially arranged close to the x-ray tube.

For an opposing magnetic field which can be well adapted to the change in the foreign magnetic field at the location of the x-ray tube to compensate for this change, the at least one compensation magnet can be controlled in its magnetic field alignment and/or its position relative to the x-ray tube.

In a further embodiment of the invention at least one permanent magnet advantageous as regards low technical outlay or low cost is provided as the compensating magnet. The magnetic field alignment of the at least one permanent magnet can be varied by a spatial rotation of its position.

Especially simply the at least one compensation magnet is able to be controlled in its magnetic field strength.

To achieve the greatest possible diversity of controllability at least one electromagnet is provided as compensation magnet; This electromagnet can be controlled both by a spatial rotation within its magnetic field alignment and also by a change electrical activation in its magnetic field strength.

If a number of compensation magnets are used, the above-mentioned types of control of the opposing magnetic field or of the compensation magnets can relate both to all magnets collectively or to each individual magnet.

Furthermore it is advantageous to provide an even number of compensation magnets arranged symmetrically in pairs in each case on opposing sides of the x-ray tube. In this arrangement of the compensation magnets the two, especially similar compensation magnets of each pair have are at the same distance from the x-ray tube and have the same or symmetrically mirrored spatial orientation so that an opposing magnetic field component generated in each case by the relevant pair is easy to calculate because of its symmetry and/or homogeneity at the location of the x-ray tube and the entire opposing magnetic field is thus easily able to be controlled. A technically especially simple further embodiment is represented here by the use of only two compensation magnets.

BRIEF DESCRIPTION OF THE DRAWINGS

The invention, as well as further advantageous embodiments of the invention in accordance with features of the subclaims, are explained in greater detail below with reference to schematic diagrams of exemplary embodiments in the drawing, without this restricting the invention to this exemplary embodiment in any way; The Figures show:

DETAILED DESCRIPTION OF INVENTION

Figure 1:
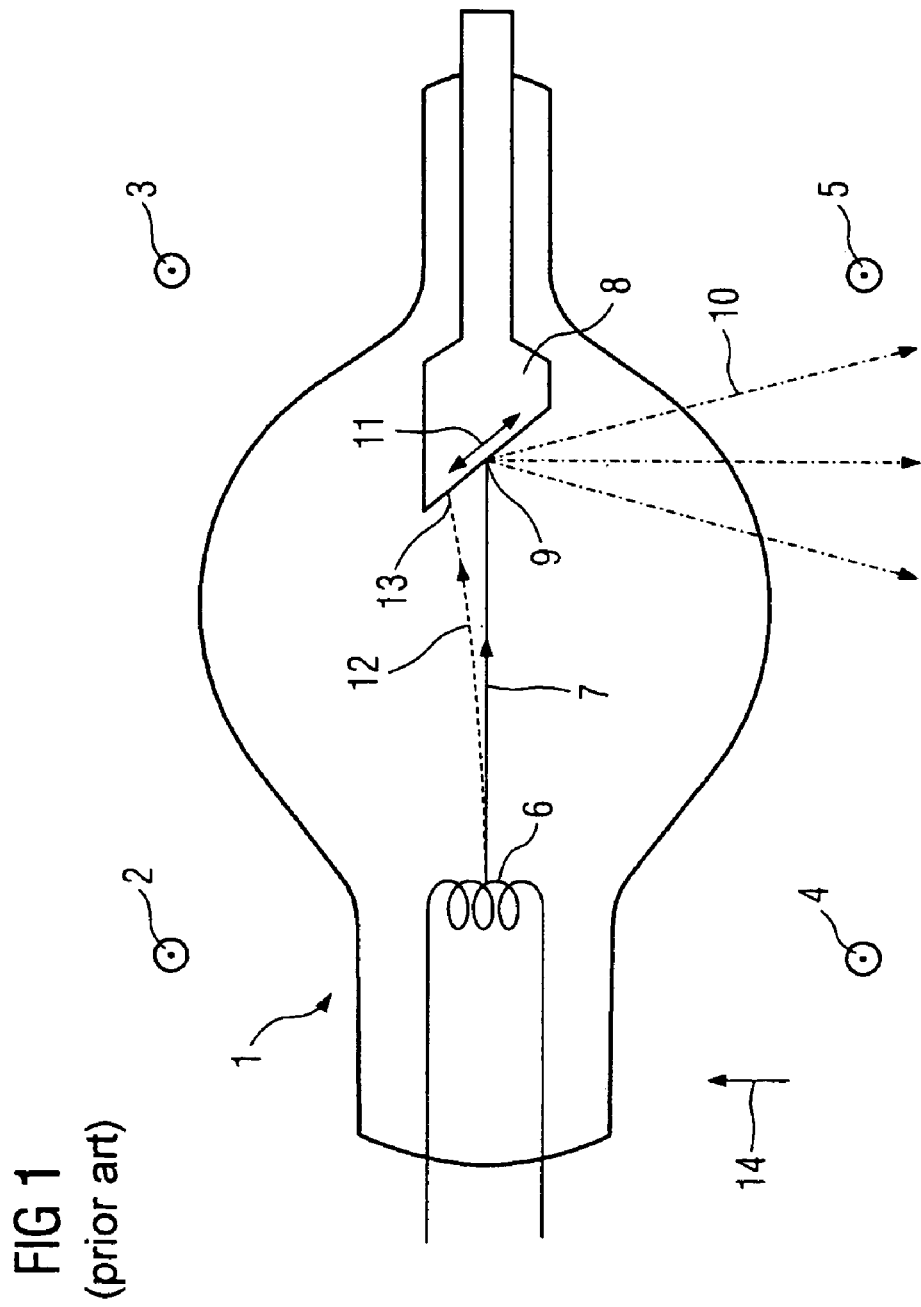
FIG. 1 to explain the underlying problem, the general layout of an x-ray tube and how it functions in a variable foreign magnetic field.

FIG. 1 shows the layout of an x-ray tube 1 known per say in accordance with the prior art in a variable foreign magnetic field essentially arranged at right angles to the plane of the diagram, which is represented by four magnetic field vectors 2-5 passing through the plane of the diagram and an operational function of the x-ray tube provided at two different points in time. At the first point in time the foreign magnetic field at the location of the x-ray tube is negligibly small so that an electron beam emitted from a cathode 6 of the x-ray tube 1 travels to an anode 8 on an essentially straight line path 7 represented by a solid line contour. The target area 9 of the electron beam on the anode 8 which is essentially in the form of a point is a source of x-ray radiation 10 and is designated as the focus.

A change in the magnetic field strength of the foreign magnetic field 2-5 causes the focus of the x-ray radiation 10 to shift on the anode in the direction of movement 11. At a second point in time the foreign magnetic field has for example become stronger such that the beam of electrons travels on an arc-shaped curved path shown by dotted line at 12 and hits a second target area 13 of the anode 8. This shifts the focus of the x-ray tube 1 and thus an x-ray image created with this x-ray tube 1 in its image section.

This previously described problem also occurs if, at the location of the x-ray tube at a first point in time, there is initially no foreign magnetic field and an if necessary also constant foreign magnetic field is only present there at the second point in time. The foreign magnetic field changing over time in this way at the location of the x-ray tube is to be understood as a variable foreign magnetic field in the sense of the invention.

Figure 2:
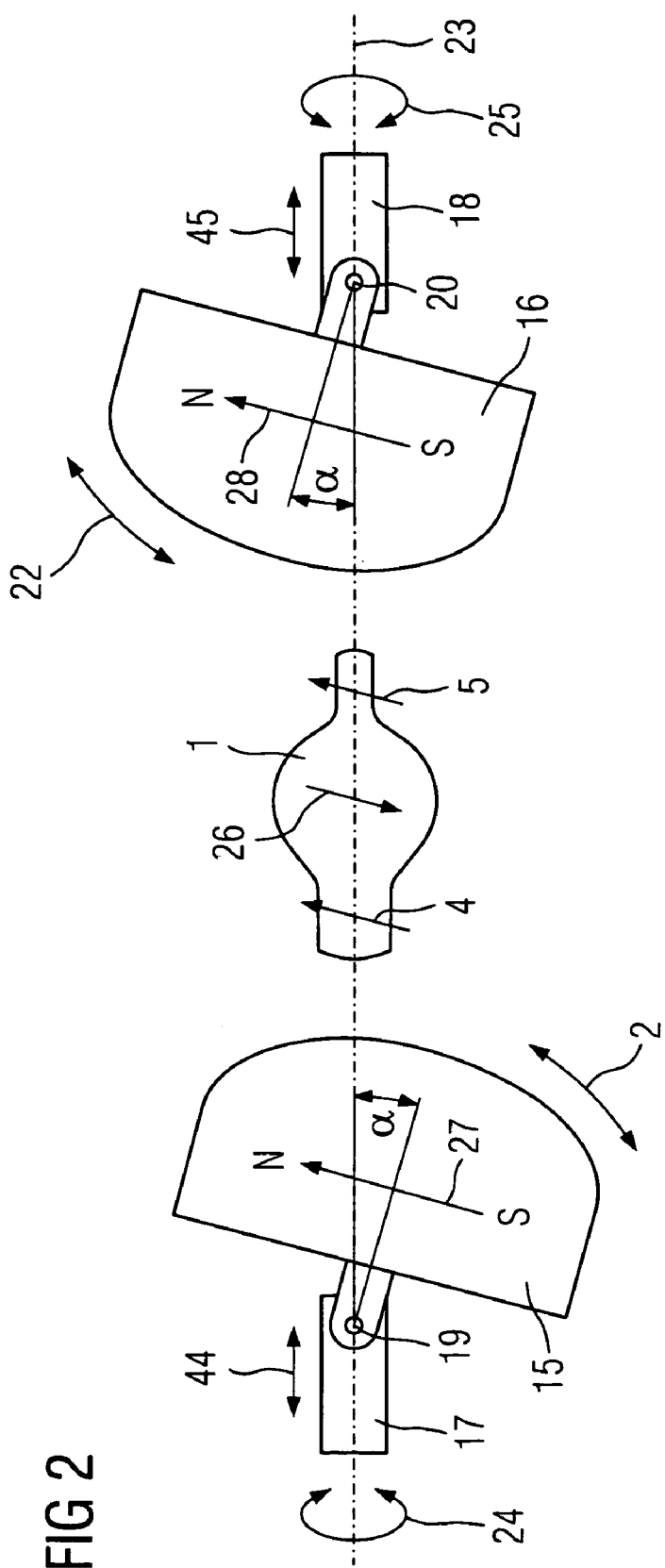
FIG. 2 an arrangement consisting of the x-ray tube in accordance with FIG. 1, shown in a reduced-size diagram, and two permanent magnets symmetrically arranged around the x-ray tube for which the alignment can be controlled, to compensate for the change in the foreign magnetic field.

FIG. 2 shows the scaled down diagram of the x-ray tube 1 in accordance with FIG. 1 seen from an angle off view 14 shown in FIG. 1, with two compensation magnets in the form of similar permanent magnets 15, 16 on opposite sides of the x-ray tube 1 being arranged at the same distance from the latter in each case. The orientation of the permanent magnets 16 can be controlled by pivoting relative to a holder 17 or 18 around a pivot axis 19 or 20 in a pivot direction 21 or 22, by rotation around a spatial axis 23 in a direction of rotation 24 or 25 and by shifting their position in a positioning direction 44 or 45 such that they compensate for the change in the foreign magnetic field 4, 5 through an opposing magnetic field 26 created by them. The relevant magnetic North pole and the relevant magnetic South pole of the two permanent magnets 15, 16 is labeled N or S respectively.

For a symmetrical arrangement and an opposing magnetic field 26 at the location of the x-ray tube 1 that can be easily calculated through this arrangement there is provision in the present exemplary embodiment for rotating the permanent magnets 15, 16, starting from a mirrored initial alignment— i.e. with a relevant pivot angle $\alpha=0$ and a parallel alignment of a relevant North-South direction 27, 28—in a same direction of rotation respectively by the same angle $\alpha$ and to rotate them in the same way around the spatial axis 23.

Figure 3:
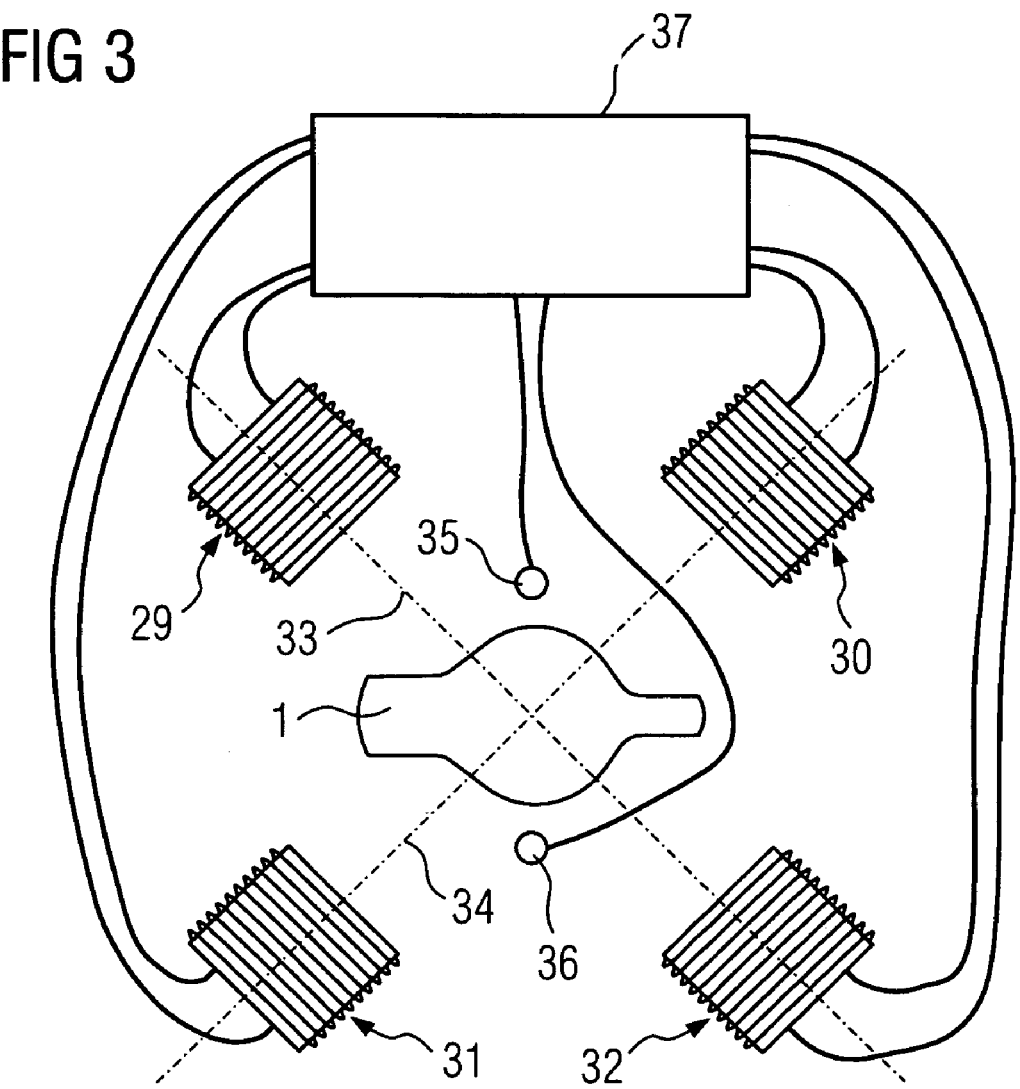
FIG. 3 an arrangement consisting of the x-ray tube in accordance with FIG. 1, shown in a reduced-size diagram, and four pairs of symmetrically arranged electromagnets on opposite sides of the x-ray tube in each case to compensate for the change in the foreign magnetic field.

FIG. 3 shows the x-ray tube 1 in accordance with FIG. 1 shown reduced in size, with four compensation magnets in the form of similar electromagnets 29-32 fixed in their position and orientation relative to x-ray tube 1 in pairs on opposite sides of the x-ray tube 1 in each case on two spatial axes 33, 34 arranged at right angles to each other at the same distance from the x-ray tube 1 in each case. To improve the clarity of the diagram further pairs of electromagnets arranged on a third spatial access which is at right angles to the two previous spatial axes 33, 34 in each case, for which there is also provision in the present exemplary embodiment, are not shown. Each of these three pairs of electromagnets 29-32 can supply an opposing magnetic field component at right angles to each other in each case at the location of the x-ray tube, so that through the overlaying of all three opposing field components an opposing magnetic field with any given magnetic field alignment and, within the context of the performance of the electromagnets 29-32, any given variable magnetic field strength can be controlled. This type of fixed arrangement of electromagnets 29-32 that can only be controlled in their relevant magnetic field strengths allows an especially wear-free but still flexible control of the opposing magnetic field.

To determine the change in the foreign magnetic field at the location of the x-ray tube 1 the foreign magnetic field is measured by two magnetic field sensors 35, 36 arranged close to the x-ray tube. Depending on this measurement a processor unit 37 controls the six electromagnets 29-32, so that the change at the location of the x-ray tube 1 is compensated for by the opposing magnetic field generated by the electromagnets 29-32.

Figure 4:
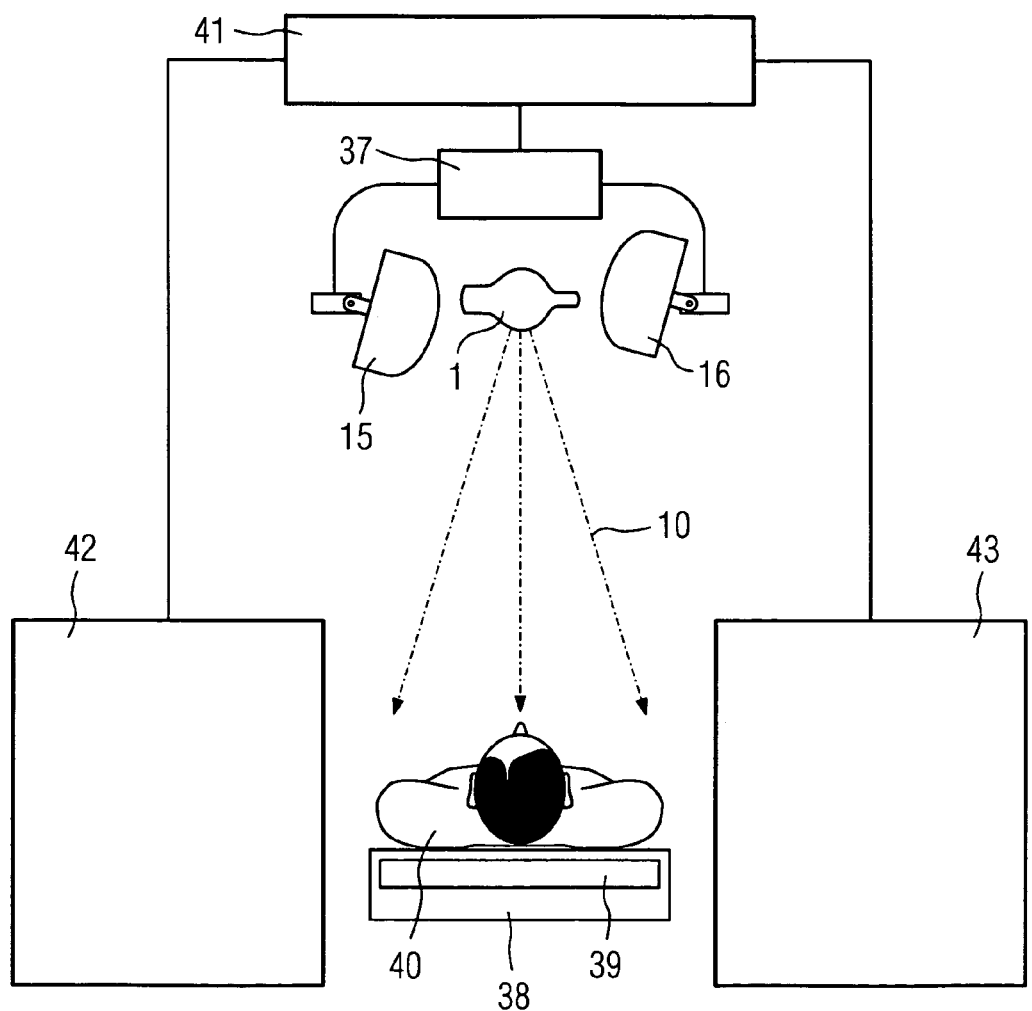
FIG. 4 the arrangement in accordance with FIG. 2, shown in a reduced-size diagram, incorporated into a treatment device for navigation of a catheter in the blood vessels or the heart of the patient by means of a foreign magnetic field.

FIG. 4 shows the arrangement in accordance with FIG. 2 reduced in size for application to an x-ray examination of blood vessels and/or of a heart of a patient 40 positioned on a patient Table 38 with an x-ray detector 13, with a catheter not shown here which can be navigated in the blood vessels and/or the heart by the variable foreign magnetic field with the foreign magnetic field been created by a two devices 42, 43 controlled by a control means in the form of a computer 41. The change in the foreign magnetic field at the location of the x-ray tube 1 is determined in this exemplary embodiment by the processor unit 37 which refers back to control data of the computer 41 and the permanent magnets 15 and 16 are controlled by the processor unit 37 in their magnetic field alignment such that the change in the foreign magnetic field at the location of the x-ray tube 1 is compensated for In this way the opposing magnetic field can be controlled in an advantageous manner simultaneously with the change in the foreign magnetic field.

In order on the one hand to be able to use small and thereby low-cost compensation magnets, here in the form of permanent magnets 15, 16 and on the other hand to cause little disturbance to the foreign magnetic field which is provided for example as here for control of the catheter, the permanent magnets 15, 16 are arranged significantly closer to the x-ray tube than the magnet creation devices 42, 43 which here jointly represent the source of the foreign magnetic field.

The invention can be summarized as follows: To enable x-ray images covering the same area in their image sections to be created in an x-ray examination despite a variable foreign magnetic field 2-5 at the location of the x-ray tube 1, there is provision in accordance with the invention to compensate for the previously determined change in the foreign magnetic field 2-5 at the location of the x-ray tube 1 by a correspondingly controlled opposing magnetic field 26; As a means for doing this, advantageously at least one compensation magnet 15, 16 or 29-32 is provided, which can be assigned to the x-ray tube 1 controllable by a processor unit 37 depending on this change.

The invention claimed is:

1. A method for x-ray examination using an x-ray tube in a variable external magnetic field, comprising the following steps:
    providing an x-ray tube;
    providing a variable external magnetic field;
    arranging the x-ray tube within the external magnetic field;
    determining a change of the external magnetic field at a current position of the x-ray tube; and
    compensating for the change of the external magnetic field by applying a compensation magnetic field, the compensation magnetic field controlled by a control mechanism based on the change of the external magnetic field.

2. The method in accordance with claim 1, wherein the compensation magnetic field is generated by at least one compensation magnet, the method further comprising controlling the compensation magnet based on the change of the external magnetic field.

3. The method in accordance with claim 1, wherein the change of the external magnetic field is determined from control data of a control unit, the control unit provided for generating the change of the external magnetic field.

4. The Method in accordance with claim 1, wherein the change of the external magnetic field is determined from magnetic field data measured by at least one magnetic field sensor.

5. The method in accordance with claim 2, wherein generating the compensation magnetic field includes controlling an alignment of the compensation magnet.

6. The method in accordance with claims 2, wherein generating the compensation magnetic field includes controlling a magnetic field intensity of the compensation magnet.

7. The method in accordance with claim 2, wherein generating the compensation magnetic field includes controlling a position of the compensation magnet relative to the x-ray tube.

8. The method in accordance with claim 1, further comprising:
    acquiring a plurality of fluoroscopy images; and
    overlaying each currently acquired fluoroscopy image with a previously recorded x-ray image.

9. The method in accordance with claim 1, further comprising:
    providing a catheter configured to be navigated by the external magnetic field; and
    navigating the catheter within a blood vessel or the heart of a patient using the external magnetic field.

10. An arrangement for x-ray examination, comprising:
    an x-ray tube configured to be moved in a variable external magnetic field;
    at least one compensation magnet assigned to the x-ray tube; and
    a processing unit connected to the compensation magnet for compensating for a change of the external magnetic field at a current position of the x-ray tube by controlling the compensation magnet to generate a compensation magnetic field.

11. The arrangement in accordance with claim 10, wherein the compensation magnet is configured to generate the compensation magnetic field in sync with the change of the external magnetic field.

12. The arrangement in accordance with claim 10, wherein the change of the external magnetic field is determined from control data of a control unit, the control unit provided for generating the change of the external magnetic field.

13. The arrangement in accordance with claim 10, further comprising a magnetic field sensor for providing measured data relative to the external magnetic field, the change of the external magnetic field determined from the measured data.

14. The arrangement in accordance with claim 10, comprising an even number of compensation magnets symmetrically arranged in pairs on opposite sides of the x-ray tube.

15. The Arrangement in accordance with claim 10, wherein the compensation magnet is arranged closer to the x-ray tube than a source generating the external magnetic field.

16. The arrangement in accordance with claim 10, wherein the compensation magnet is a permanent magnet.

17. The arrangement in accordance with claim 16, wherein generating the compensation magnetic field includes controlling an alignment of the permanent magnet.

18. The arrangement in accordance with claim 10, wherein the compensation magnet is an electromagnet.

19. The arrangement in accordance with claim 10, wherein generating the compensation magnetic field includes controlling a magnetic field intensity of the compensation magnet.

20. The arrangement in accordance with claim 18, comprising a plurality of electromagnets having a fixed arrangement and orientation relative to the x-ray tube, the plurality of electromagnets configured to be controlled exclusively regarding their respective magnetic field intensity.

* * * * *